United States Patent [19]

Langford

[11] Patent Number: 5,184,633
[45] Date of Patent: Feb. 9, 1993

[54] CLEANSING AND STERILIZATION MECHANISM SUITABLE FOR CONTACT LENSES AND THE LIKE

[75] Inventor: Terrence R. Langford, Tucson, Ariz.

[73] Assignee: KEW Import/Export Inc., Tucson, Ariz.

[21] Appl. No.: 774,047

[22] Filed: Oct. 8, 1991

Related U.S. Application Data

[63] Continuation-in-part of Ser. No. 556,570, Jul. 20, 1990, abandoned.

[51] Int. Cl.$^5$ .............................................. B08B 3/10
[52] U.S. Cl. .............................. 134/57 R; 134/102.1; 134/901; 422/116; 422/186.08; 422/292; 422/305
[58] Field of Search ............... 134/57 R, 58 R, 102, 134/901; 422/29, 116, 186.07, 186.08, 186.1, 292, 305

[56] References Cited

U.S. PATENT DOCUMENTS

| 3,621,855 | 11/1971 | Rabinowitz | 134/901 X |
|---|---|---|---|
| 3,720,402 | 3/1973 | Cummins et al. | 134/901 X |
| 3,801,278 | 4/1974 | Wagner et al. | 422/116 |
| 4,063,890 | 12/1977 | Baron | 422/24 |
| 4,143,116 | 3/1979 | Meltzer | 422/116 |
| 4,228,136 | 10/1980 | Thomas | 134/901 X |
| 4,381,285 | 4/1983 | Wittenberg | 422/116 |
| 4,568,517 | 2/1986 | Kaspar et al. | 134/143 X |
| 4,746,489 | 5/1988 | Arnold | 422/29 |
| 4,782,946 | 11/1988 | Pollak | 134/901 X |
| 4,863,698 | 9/1989 | Ryder et al. | 422/116 |
| 5,051,137 | 9/1991 | Nold | 422/186.08 X |

FOREIGN PATENT DOCUMENTS

0000620 9/1979 PCT Int'l Appl. ................. 422/116

Primary Examiner—Philip R. Coe
Attorney, Agent, or Firm—Ogram & Teplitz

[57] ABSTRACT

A cleansing and sterilization mechanism which is usable on contact lenses, surgical instruments, dental tools, and other items which require regular cleansing and sterilization. Using ozone as the cleansing and sterilization medium, the apparatus provides for added guaranty of operation through the use of feedback mechanism to assure that all the components are working and that the to-be-cleaned items are exposed to the ozone bath for the specified time. Furthermore, the item is capable of communicating, via phone line, to a central unit which monitors the operation and performance of the mechanism.

41 Claims, 3 Drawing Sheets

CLEANSING AND STERILIZATION MECHANISM SUITABLE FOR CONTACT LENSES AND THE LIKE

This is a continuation-in-part of U.S. patent application Ser. No. 07/556,570, entitled "A Contact Lense Cleaning Device and Method" filed Jul. 20, 1990, and now abandoned.

BACKGROUND OF THE INVENTION

This invention relates generally to cleansing and sterilization of items and more particularly to the cleansing and sterilization of items through the use of ozone.

Although this invention has tremendous applications to a variety of items to be cleaned including but not limited to, dental tools, surgical instruments, implants, etc., for an understanding of the problems associated with cleansing and sterilization, the following discussion focusses on the cleansing and sterilization of contact lenses.

The success or tragic failure of contact lens wear is ultimately determined by the care and aseptic handling of the lenses. With over seventeen million contact lens wearers in the United States spending two billion dollars on contact lens supplies, a simple one step cleaning and sterilizing process is sought. Both hard and soft lenses currently need daily, or in the case of extended wear contacts, weekly cleaning and antiseptic treatment.

By their very nature, being in close relationship with the wearer for extended periods of time, contact lenses are susceptible to both: buildups of protein and lipids from the wearer; and also from contamination from microorganisms. Either of these, buildup or contamination, can have debilitating affects such as reduced vision, scarring of the eye, and even blindness.

Hydrophilic contact lenses, being soft and composed mainly of water, have made the problem of cleaning even more difficult. Physical pressure on the hydrophilic lense may cause rips; strong disinfectants become lodged within the body of hydrophilic lense itself and then irritate the wearer's eye causing an ulcer.

Without a good cleaning process, both the hard and soft contact lense is susceptible to a wide variety of contaminating microorganisms including: Acanthamoeba, Pseudomonas organisms, Alcaligenes faecalis, staph. Aureus, and Enterobacter aerogenes.

For a through understanding of the diseases associated with contact lenses, see: "Pseudomonas aeruginosa Contamination of Hydrophilic Contact Lenses and Solutions", by Milauskas, appearing in *Transactions of the American Academy of Ophthalmology and Otology*, vol. 76, March-April 1972, page 511; "Complications Associated with Contact Lens Solutions", by Morgan, appearing in *Ophthamology AAO*, vol. 86, June 1979, page 1107; "The Soft Plastic Contact Lenses", by Dastoor, appearing the *Indian Journal of Ophthamology*, vol XXI, on page 25; "Microbiological Evaluation of Soft Contact Lens Disinfecting Solutions" by Houlsby et al., appearing in the *Journal of the American Optometric Association*, vol. 55, Number 3, page 205; and, "Susceptibility of Acanthamoeba to Soft Contact Lense Disinfection Systems", appearing in the *Investigative Ophthamology & Visual Science*, April 1986, Vol. 27, page 626.

Additionally, the high water content of hydrophilic contact lenses make them more susceptible to the formation of "jelly bump" deposits which are composed primarily of lipids and calcium. These lipid formations are usually long and intermediate chain cholesterol esters and triglycerides which are particularly difficult to remove from a soft lens without damaging the lense. A good review of this problem is "Origin and Composition of Lipid Deposits on Soft Contact Lenses" by Hart et al., and appearing in *Ophthamology*, April 1986, vol. 93, No. 4, page 495.

The typical method of cleaning, using a saline solution and distilled water approach has not been totally satisfactory. It has been found though that this approach does not truly address the contamination problem; indeed, several of the contaminating microorganisms actually thrive in the cleaning environments.

Because of this, the industry has been seeking alternative cleaning approaches which may be used by the wearer, not a laboratory.

One technique proposed is the use of a 3% hydrogen peroxide solution for the cleaning and disinfecting the lenses. The reason for this popularity is that after disinfecting, the hydrogen peroxide is converted into innocuous by-products which are compatible with ocular physiology.

The hydrogen peroxide approach is well described in: "A Comparison of New Hydrogen Peroxide Disinfection Systems" by Krezanoski et al., and appearing in the *Journal of the American Optometric Association*, vol. 59, No. 3, page 193; "Efficacy of Hydrogen Peroxide Disinfection Systems for Soft Contact Lenses Contaminated with Fungi", by Penley et al., and appearing in the *CLAO Journal*, January 1985, vol. 11, no. 1, page 65; "Reaction to Hydrogen Peroxide in a Contact-Lens Wearer", by Knopf, appearing the *American Journal of Ophthamology*, June, 1984, page 796; "Hydrogen Peroxide in Anterior Segment [Physiology: A Literature Review", by Chalmers, appearing in *Optometry & Vision Science*, page 796; and, "Hydrogen Peroxide Sterilization of Hydrophilic Contact Lenses", by Gasset et al., and appearing in *Arch. Ophthamology*, vol. 93, June 1975, page 412.

Unfortunately, hydrogen peroxide, at the 3% level or even the 6% level, is incapable of disinfecting some of the hardier microorganisms. Further, hydrogen peroxide does not have any noticeable affect upon the "jelly bumps".

Perhaps the most common treatment is the heat method. In this approach the contact lenses are exposed to a temperature of eighty degrees centigrade for a period ten minutes. This approach is more effective than chemicals against microorganisms but the treatment substantially decreases the life of the contact lenses and is usable only with about half of the present contact lenses. Use of this method depends heavily upon the water content and the type of plastic used in the lenses' construction.

Additionally, proteins and other contaminants that are left in the contact lense (buildup) can substantially produce irritation in the eyes of the user.

It is clear from the foregoing that an efficient and through cleaning technique does not exist for contact lenses.

SUMMARY OF THE INVENTION

A cleansing and sterilization mechanism which is usable on contact lenses, surgical instruments, dental tools, and other items which require regular cleansing and sterilization. Using ozone as the cleansing and sterilization medium, the apparatus provides for added guaranty of operation through the use of feedback mechanism to assure that all the components are working and that the to-be-cleaned items are exposed to the ozone bath for the specified time. Furthermore, the item is capable of communicating, via phone line, to a central unit which monitors the operation and performance of the mechanism.

Fundamentally the present invention consists of a housing having therein an ozone generator, a pump, and a controller. A container holding the items to be sterilized and cleansed is instertable into the housing. The controller assures that both the pump and ozone generator are operating. Via valves in the container, ozone is directed over the to-be-cleaned items forming an ozone bath. After the proper amount of time has elapsed, the controller either shuts down the pump and ozone generator, or the controller redirects the ozone to another container (depending on the embodiment in use).

The container, with the now sterilized items, is removable from the housing and may be carried with the user or moved to a location where the items will be used (i.e. in an operating theatre, moved to the operating table). The items within the container are kept sterile through the use of self-sealing valves which seal when the container is removed from the housing.

Although the present invention relates to a variety of items, the application of cleansing of contact lenses is one of the major applications. Because of this, the following discussion relates to the present invention's application to this field.

An ozone generator creates a bath of ozone and saline. A cage or other suitable arrangement, submerges the contact lenses into this bath for a predetermined amount of time. A timer either deactivates the ozone generator at the proper time or alerts the user so that the contact lense should be removed from the bath.

Ozone was discovered in 1840 by Christian Friedrich Schonbein. Ozone is three oxygen atoms bonded together. Unfortunately, ozone has a very short life, usually about twenty minutes. As the ozone breaks down, its natural by products are pure water and stable oxygen.

It is the off-gas ozone which has created the largest concern for health reasons. Standards for the protection of users range in the 0.10 to 0.12 parts per million range.

Because of ozone's ability to control bacteria and virus microorganisms, ozone has been used since the 1890's to purify water for drinking. More recently, ozone has been used in swimming pools to reduce the dependency on chemical purification.

Production of ozone is typically created by passing air past an ultraviolet light in a sealed chamber. This produces an ozone-rich air which is then pumped into a saline bath.

Sterilization using ozone is effective for all ocular pathogens including viruses, bacteria, fungus, and most importantly amoebae. The time of actual ozone exposure to the contact lenses is less than or equal to the present method of heat or chemical aseptisizing, usually ten minutes.

Ozone is the second most powerful oxidant known. This means that ozone: is a powerful oxidant for pollutants and organic contaminants; and, is an excellent sterilant for microorganisms. When compared to chlorine, ozone has an oxidizing potential 50% greater and can destroy bacteria and viruses up to three thousand times faster.

Ozone is also a strong oxidizing agent which causes small suspended particles to coagulate and precipitate away from the contact lenses. This assists in the cleaning of the contact lenses since removed matter is quickly and effectively removed from the proximity of the contact lense.

Two different levels of the present invention are envisioned: the first is a home-use apparatus for the cleaning of a single pair of contact lenses; the second is an eye care practitioner's office apparatus for the production cleaning of multiple contact lenses.

The invention is particularly powerful for the home use application. In this situation, the main part which fails in the cleansing and contact lenses is the user himself. Typically, the user forgets to cleanse the contact lense and then "swears" to his doctor that the cleansing was done religiously.

In certain countries, especially European countries, the responsibility of assuring that the user does clean the contact lenses falls upon the physician. Because of this, the physician wants to be sure that i) the user is using the device, and ii) the user will return to the physician regularly for follow-up examinations.

In the preferred embodiment, the present invention accomplishes these objectives by having a prescribed number of "cleanings/sterilizations" logged onto a memory chip. The user is able to use the device only this many times and then must return to the physician to have the use data reestablished. Furthermore, the physician is able to poll the device, via the phone lines, as to the actual number of uses the user has made of the device.

In operation, the preferred embodiment of the invention:

1) The power is turned on to the unit by the user;
2) The on-board computers checks to see if the pump and ozone generator lamp are off;
3) The computer checks to see how many counts are remaining in the memory count-down;
4) Based upon these checks, the computer,
   a) If the count is zero, the computer notifies the user via such devices as flashing Light Emitting Diodes (LEDs) and shuts down the operation, or,
   b) If the count is under a predermined warning level (i.e. 10), then the operator is notified via the LEDs and the ozone generator and pump are activated, or,
   c) If the count is above the warning level, the computer notifies the user via the LEDs and the ozone generator and pump are activated;
5) The computer waits a short period of time (i.e. 300 milliseconds) and checks to see that the pump and light are activated;
6) The computer waits another short period of time (i.e. 1 second) and checks to see if gas flow is detected [note- steps 5 and 6 are safety checks to see if the apparatus is working];
7) After the prescribed amount of time (i.e. 19 minutes) the computer shuts off the ozone generator permitting the pump to continue operation to purge the system; and,
8) After the ozone generator is deactivated, the pump operates a short period (i.e. 1 minute) before the computer deactivates the pump.

Studies conducted have found that using an ozone generator producing 0.02 grams of ozone per hour requires a submersion of 3 minutes for a thorough cleaning.

In an enhanced embodiment, the contact lenses are automatically removed from the ozone bath at the termination of the proper elapsed time and the ozone generator is switched "off". Once removed from the ozone bath, the contact lenses are rinsed with a saline solution, permitting any ozone which may have impregnated the lenses, particularly hydrophilic contact lenses, to break down into harmless elements.

The preferred embodiment of the present invention utilizes an ozone generator producing from 0.01 grams to 1 gram of ozone per hour. This is the preferred level since it reduces any health dangers which might occur from air-suspended off-gassed ozone. Those of ordinary skill in the art readily recognize how to construct an ozone generator having this capability.

Those of ordinary skill in the art acknowledge the use of two procedures to produce ozone: ultraviolet radiation; and, corona discharge.

Most ozone generators currently use ultraviolet radiation. These are usually the lowest cost ozone generators on a per unit basis. This decrease in cost is due to the fact that the air does not go through an initial drying process.

Newer units being produced utilize a corona discharge technique which dry the air before charging the air with ozone. This drying permits the corona discharge apparatus to produce a higher ozone concentration.

For minimal expenditures of electrical energy, ozone normally is produced from dried air ($-60$ degrees fahrenheit dew point) in concentrations of one to two percent and from dry oxygen in concentrations of two to four percent. More than eighty percent of the electrical energy applied to the electric discharge field is converted to heat and, if this is not quickly removed from the cell, the heat causes rapid decomposition of the ozone back to oxygen. The rate of this reverse reaction increases rapidly above thirty-five degrees centigrade. Proper cooling of the ozone generator cells is critical to maintaining consistent yields of ozone.

For the second type of apparatus, that of a production cleaning device in an eye care practitioner's office, multiple containers are used for cleaning several sets of contact lenses simultaneously (or alternatively for cleaning several sets of surgical instruments or dental tools). In this application the controller also detects when a container is placed with a slot in the housing and then operates on the multiple containers on a first come-first served approach.

If the ozone generator is sufficiently large, then multiple containers may be cleansed/sterilized simultaneously.

For both versions, the air flow is generated by a bellows type low pressure pump. Those of ordinary skill in the art readily recognize other pumps which will serve this function.

Also, for all the applications, the containers are automatically sealed upon removal from the housing. This is accomplished by any of several mechanisms well known to those in the art.

This feature, of sealing upon removal, permits the transportation of the contact lense, or other such device, without fear of contamination. In the preferred embodiment, when the lid to the container is opened, this opening shifts an indicia so that, later, the user is able to determined that the container has been opened and that the items are no longer considered sterile.

In the production cleaning embodiment, the ozone generator preferably produces 0.01 grams to 5 grams of ozone per hour.

One important attribute of the present invention is its ability to provide a variety of levels of "cleaning". It has been found that by varying the amount of ozone and the amount of elapsed time of exposure, contact lenses may be disinfected, asepticized, or even sterilized. None of the current state of the art devices can achieve these results without damaging the contact lenses or producing harmful effects to the eye.

The invention, together with various embodiments thereof will be more fully described by the following drawings and their accompanying descriptions.

DRAWINGS IN DETAIL

Figure 1:
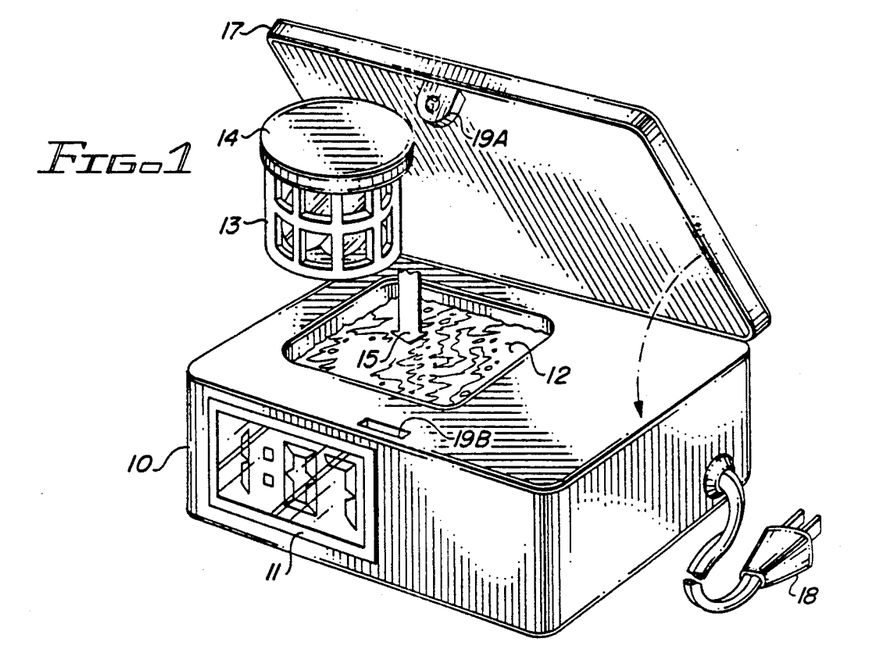
FIG. 1 is a perspective view of a personal use embodiment of the invention.

FIG. 1 is a perspective view of a personal use embodiment of the invention. This embodiment is intended to be used by the contact wearer to periodically clean and disinfect their own contact lenses at home.

Contact lense cleaner 10 receives its power via electrical cord 18 which utilizes household electrical current. This electrical current is used to power clock 11 and the ozone generator (not shown). Clock 11 is a countdown type of clock showing the remaining time necessary for proper cleaning the contact lenses.

The contact lenses are placed in cage 13. To facilitate easy placement of the lenses within cage 13, removable top 14 permits access to the interior portion of cage 13. Cage 13, once the contact lenses are placed therein, is lowered, as illustrated by arrow 15, into basin 12 (having saline therein) and lid 17 is closed, as illustrated by arrow 16.

The closing of lid 17 causes latch 19A to enter receptacle 19B which signals clock 11 that the contact lenses are suitable placed within basin 12. Clock 11 then activates the ozone generator (not shown) to create a bath of ozone and saline within basin 12.

When the selected amount of time has elapsed, clock 11 deactivates the ozone generator and releases lid 17 by latch 19a. The raising of the lid signals the user that the contact lenses are clean and ready for rinsing and use.

In one embodiment of this invention, cage 13 is removable and has a protrusion which supports it above basin 12. This permits the enclosed contact lenses to drip dry and also provide a time lapse for any absorbed ozone to convert to its benign by-products before the user again places the contact lenses within their eyes.

It has been found that through control of the amount of ozone and the amount of time of exposure, contact lenses may not only be cleaned but either disinfected, asepticized, or even sterilized. Control of these factors, amount of ozone and elapsed time, depends upon the manufacturer and user to obtain the desired results.

Figure 2:
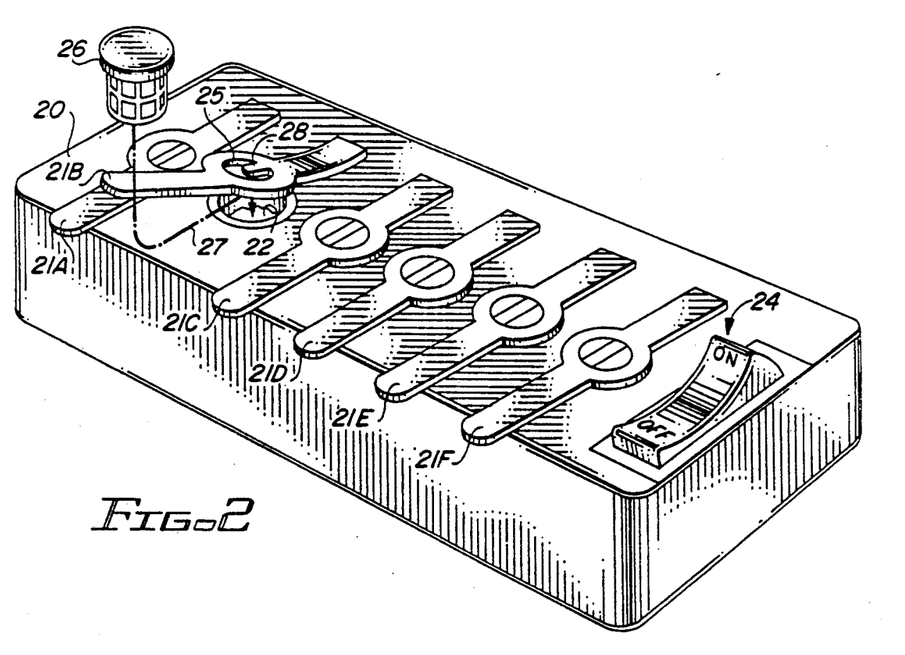
FIG. 2 is a perspective view of a production use embodiment of the invention.

FIG. 2 illustrates an embodiment of the invention for production cleaning. This embodiment is wired into the electrical current of the shop and is activated by a simple on/off switch 24.

Once activated, the bath of ozone and saline contained within unit 20 is created and is constantly fed ozone until the work shift is completed or when the task is completed.

A plurality of holders (21A, 21B, 21C, 21D, 21E, and 21F) are used to clean contact lenses in parallel. Each holder, such as holder 21A, maintains the cage holding the contact lenses in the bath. When the appropriate time has elapsed, the holder raises the cage from the bath.

In this example, holders 21A, 21C, 21D, 21E, and 21F all have cages (such as cage 23 for holder 21A) emersed in the bath. Holder 21B has raised indicating to the operator that cage 26 must have its existing contact lenses removed and another set secured therein.

Once the unclean contact lenses are secured within cage 26, the cage is placed in orifice 25 on holder 21B as indicated by arrow 27. Keeper 28 secures cage 26 in position; the handle of holder 21B is then pushed down forcing secured cage 26 into bath 22.

Keeper 28 is used in this embodiment to secure cage 26 within holder 21B. In another embodiment of the invention, keeper 28 is timed controlled to prevent removal of cage 26 before an allotted amount of time has elapsed for proper drying of the contact lenses.

Those of ordinary skill in the art readily recognize various mechanisms which will work as timing devices for holders 21A, 21B, etc. such as: electronic clocks linked to the holder; spring timed mechanism; and the like.

This embodiment of the invention also illustrates the mechanism which may be used for the personal cleaning apparatus. A mechanism with a single holder is suitable for use by a single user.

Figure 3:
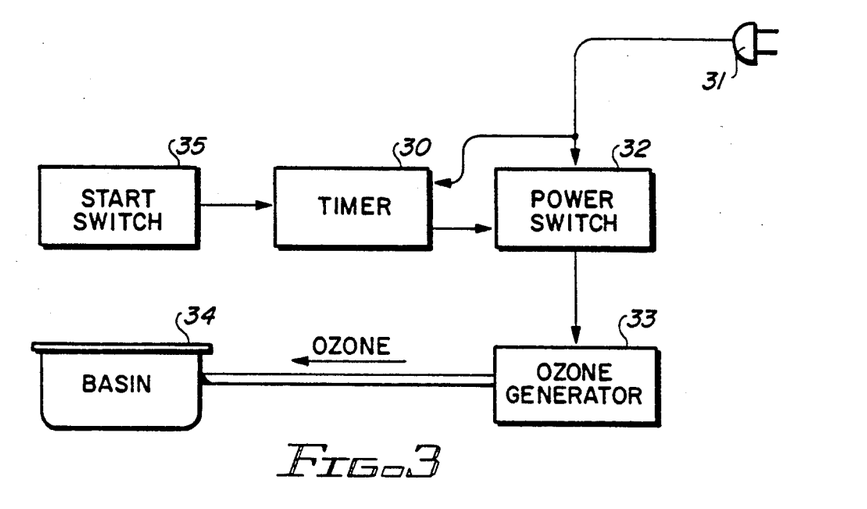
FIG. 3 is a block diagram illustrating the operation of an a personal use embodiment of the invention.

FIG. 3 is a block diagram of the operation of an embodiment of the invention. Electrical power is supplied via plug 31 to power switch 32 and timer 30.

Start switch 35 informs timer 30 when the cage holding the contact lenses is properly positioned. Start switch 35 may be a variety of switches well known in the art including the latch switch first illustrated in FIG. 1, a manually operated switch, or any other well known to those in the art.

Once start switch 35 is activated, timer 30, activates ozone generator 33 via power switch 32. Ozone generator provides ozone to basin 34, with saline therein, until such time as timer 30 deactivates the ozone generator 33 by denying electrical power through power switch 32.

It is clear from the foregoing that in this embodiment of the invention, timer 30 acts as a controller for the entire operation of the mechanism.

Figure 4:
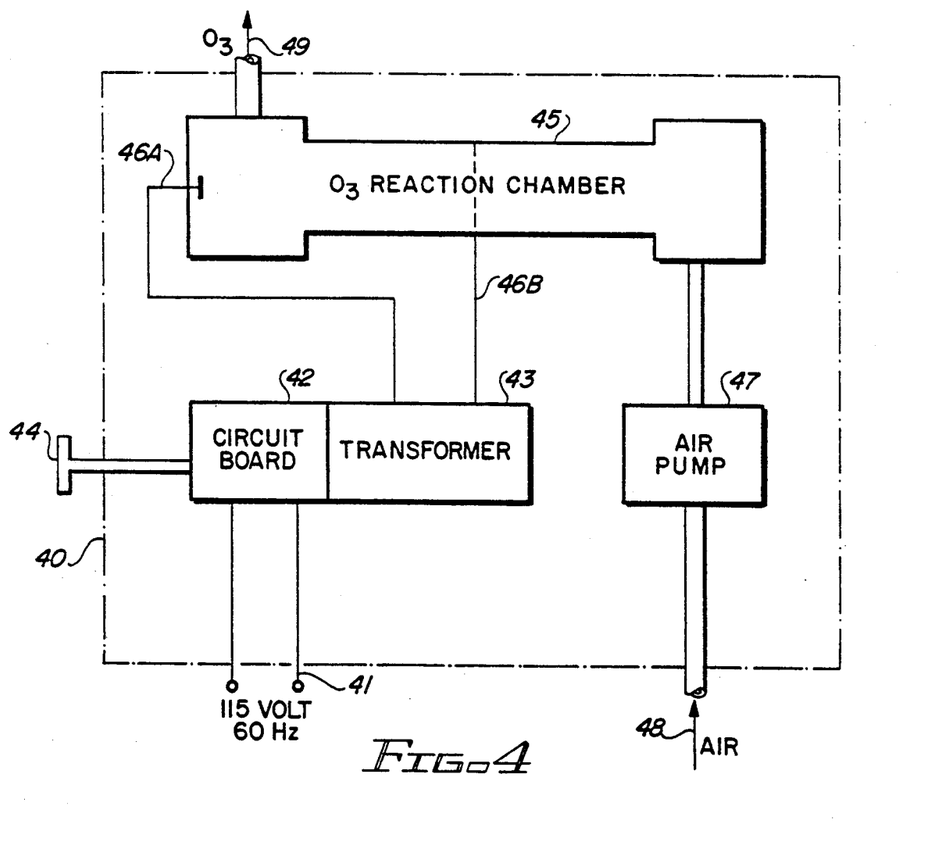
FIG. 4 is a block diagram of the preferred embodiment of the ozone generator.

FIG. 4 is a block diagram of the preferred ozone generator for the invention. Ozone generator 40 receives standard electrical energy 41 being 115 volts at 60 hertz. This electrical energy passes through circuit board 42 and is modified to drive transformer 43 at the prescribed rate as determined by operator adjustment knob 44. Utilizing the operator adjustment know 44, the operator is able to vary the concentration of ozone being produced by ozone generator 40.

Leads from transform 43 feed a cathode 46A and anode 46B positioned within the ozone reaction chamber 45. Ozone reaction chamber 45 is preferably constructed of stainless steel and has a glass dielectric therein.

Air pump 47 draws in outside air 48 into the system and through ozone reaction chamber 45 producing a flow of ozone 49.

Those of ordinary skill in the art readily recognize alterations which may be made to the present layout to permit this embodiment to be utilized in a variety of settings and for a variety of ozone demands.

Figure 5:
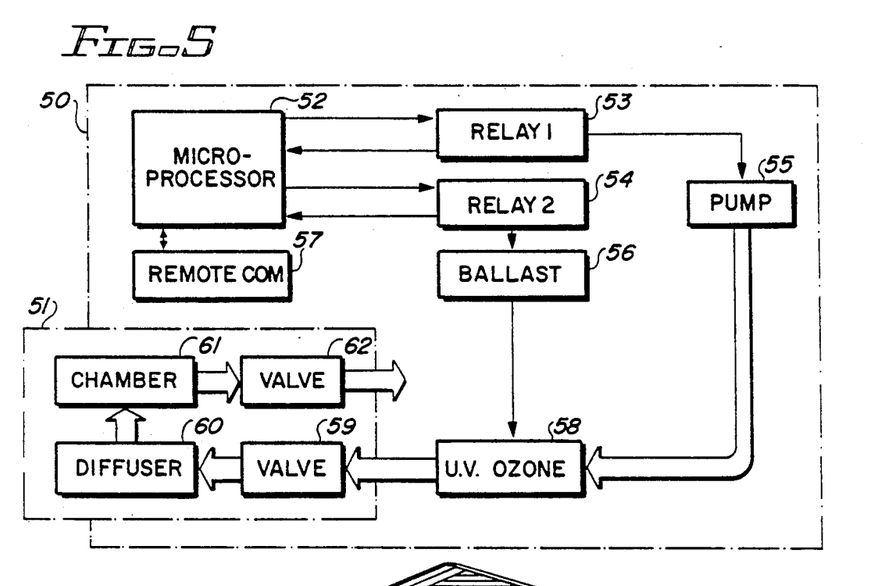
FIG. 5 is a block diagram illustrating the interaction of the components for the preferred embodiment of the contact lense cleanser/sterilizer.

FIG. 5 is a block diagram illustrating the interaction of the components for the preferred embodiment of the contact lense cleanser/sterilizer.

Main unit 50 receives electrical power (not shown) via a typical house outlet of 110 volt. Microcomputer 52 acts as a controller for the entire unit. By activating relay 1, microcomputer 52 is able to activate pump 55; by activating relay 54, microcomputer is able to activate ballast 56 which energizes the Ultraviolet ozone generator 58.

Air flow from pump 55 is passed through the ozone generator 58 and ozone is created. The ozoniated air flow passes into container 51 via valve 59. Ozone bubbles within the air flow are broken into small bubbles via diffuser 60. Diffusion of the ozone increases the surface area of the ozone and thereby increases the overall effectiveness.

The diffused ozone air flow passes through chamber 61 where the items to-be-cleaned are placed. Finally, the ozone air flow is exhausted via valve 62.

Both valve 59 and valve 62 seal when container 51 is removed from housing 50. Container 51 keeps the contact lenses, or other items, sterile until container 51 is opened.

Microcomputer 52 is able to communicate with a remote computer (not shown) via remote communication link 57. In the preferred embodiment, this remote communication link is a modem type device although those of ordinary skill in the art readily recognize various other mechanism which will serve this purpose.

Memory, located in this embodiment within microcomputer 52, is nonvolatile permitting a constant upgrade of the operational data and also of the time parameters and usage of the device. This information is easily communicated via the remote communication link 57.

Additionally, remote communication 57 permits a remote computer, such as in a physician's office, to reset the device permitting the operator to use the device once his alloted amount of uses has been completed. This practice assures the physician that the user is actually using the device and also forces the user to come in for scheduled reexamination to assure that the contact lense is not causing some unforeseen damage to the eye.

Microcomputer 52 is able to monitor, via sensors (not shown) the operation of pump 55, ballast 56, ozone generator 58, and that container 51 is securely placed within housing 50. So long as everything is operating within specifications, microcomputer operates the assemblage until the predetermined amount of time has elapsed.

Should one of the components malfunction, then microcomputer terminates operation and informs the operator of the aborted operation.

Should the application require, a filter is added to valve 62 to trap excess ozone from entering the atmosphere.

Figure 6:
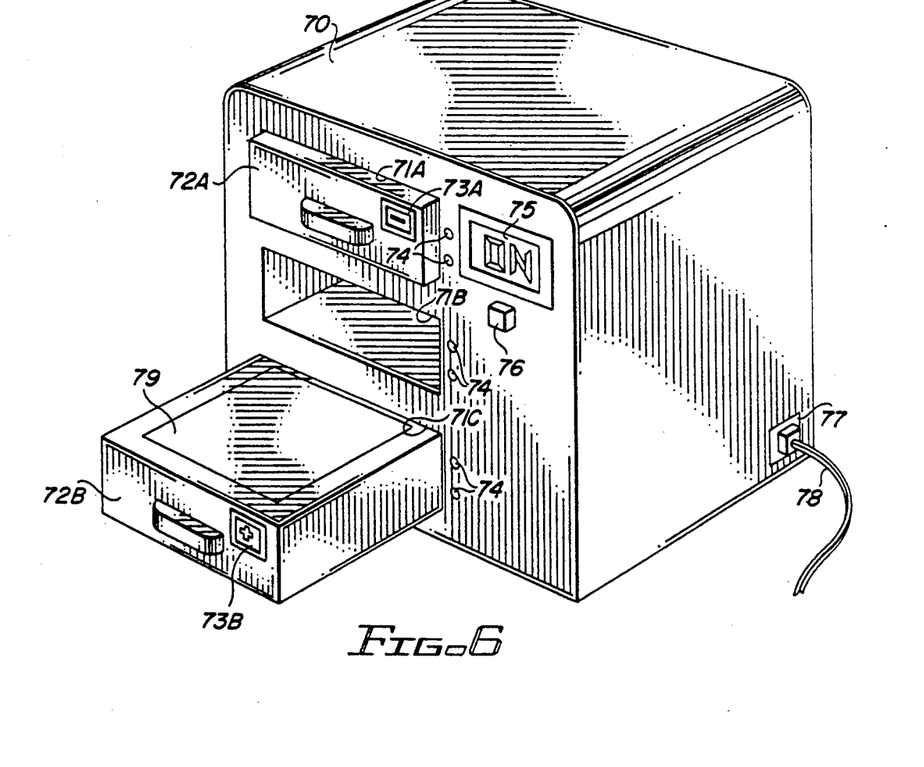
FIG. 6 is a perspective view of an embodiment of the invention utilizing multiple container capability.

FIG. 6 is a perspective view of an embodiment of the invention utilizing multiple container capability.

Housing 70 contains multiple slots 71A, 71B, and 71C. Although this embodiment illustrates three slots, those of ordinary skill in the art readily recognize that any number of slots is possible.

Into these slots are inserted containers 72A and 72B. Note that slot 71B is empty at the present time. In this embodiment, once a container has had its contents sterilized, it may be removed and stored without contaiminating the contents since the valves (not shown) are self-sealing and lid 79 is also sealed.

As an added contamination safeguard, indicators 73A and 73B are used to indicate if the contents are sterile or not. The microcomputer (not shown) moves indicator 73B to a "+" indicating that the sterilization process in complete; opening of the the lid moves indicate to a "−" (as shown in 73A. In this fashion, a sterile container is easily identified.

Status display 75 is used by the microcomputer to communicate with the operator. Switch 76 permits the operator to activate/deactivate the device.

Communication with remote computers is facilitated via modular jack 77 and phone line 78.

It is clear from the foregoing that the present invention provides for new and improved cleaning for contact lenses.

What is claimed is:

1. A contact lense cleaning system having:
   a) a housing;
   b) an ozone generator for producing ozone, said ozone generator located within said housing;
   c) a contact lense container being insertable into said housing;
   d) a pump for transferring ozone from said ozone generator to said contact lense container, said pump being located in said housing;
   e) a switch located on said housing for operator activation;
   f) means for sensing operation of said ozone generator and generating an ozone operating signal having at least two states;
   g) means for sensing operation of said pump and generating a pump operating signal having at least two states; and,
   h) control means for,
      1) activating said pump and said ozone generator in response to activation of said switch, and,
      2) deactivating said pump and said ozone generator in response to the states of to said ozone generating signal and said pump generating signal.

2. The contact lense cleaning system according to claim 1 wherein said control means further includes:
   a) clock means for determining elapsed time from activation of said pump and said ozone generator; and,
   b) means for deactivating said pump and said ozone generator when the elapsed time is equal to a predetermined level.

3. The contact lense cleaning system according to claim 2 further including means for receipt of electrical power to said lense cleaning system, and wherein said control means further includes:
   a) means for sensing a power failure to said contact lense cleaning system; and,
   b) means for initalizing said clock means upon restoration of power to said contact leanse cleaning system.

4. The contact lense cleaning system according to claim 3 further including a non-volatile memory means and wherein said control means includes means for recording, in said memory means, usage data indicative of operation of said contact lense cleaning system.

5. The contact lense cleaning system according to claim 4 further including communication means for receipt of command data and transmission of usage data via a telephone line and wherein said control means includes means for transmitting said usage data from said memory in response to said command data.

6. The contact lense cleaning system according to claim 5 wherein said memory means further includes use counter data and wherein said control means includes:
   a) means for, prior to activation of said pump and said ozone generator, comparing said use counter data with said usage data; and,
   b) means for terminating operation if said usage data equals or exceeds said counter data.

7. The contact lense cleaning system according to claim 1 wherein said contact lense container includes:
   a) a first valve being automatically sealed upon removal of said contact lense container from said housing, said first valve for receipt of ozone from said pump; and,
   b) a second valve being automatically sealed upon removal of said contact lense container from said housing, said second valve permitting excess ozone within said container to pass into the enironment.

8. The contact lense cleaning system according to claim 7 wherein said contact lense container includes a sealable opening for putting contact lenses into said contact lense container.

9. The contact lense cleaning system according to claim 7 further including an ozone trap interposed between said second valve of said contact lense container and the environment.

10. The contact lense cleaning system according to claim 1 further including:
    a) a liquid agent contained in said contact lense container; and,
    b) a diffuser, located in said contact lense container, for diffusion of said ozone in said liquid agent.

11. The contact lense cleaning system according to claim 10 wherein said diffuser includes at least one flat plate diffuser.

12. The contact lense cleaning system according to claim 1 wherein said ozone generator includes an ultraviolet lamp for generation of said ozone.

13. The contact lense cleaning system according to claim 12 wherein said ultraviolet lamp is U shaped and further including a chamber encirculing said ultraviolet lamp, said chamber having a first end open for receipt of ambient air from said pump and a second end communicating with said first valve of said contact lense container.

14. A contact lense cleaning system having:
    a) a housing;
    b) an ozone generator for producing ozone, said ozone generator located within said housing;
    c) a contact lense container being insertable into said housing and in communication with said ozone generator via a valve; and,
    d) a pump for transferring ozone from said ozone generator to said contact lense container, said pump being located in said housing.

15. A contact lense cleaning system having:

a) a housing;
b) an ozone generator for producing ozone, said ozone generator located within said housing;
c) a contact lense container being insertable into said housing;
d) a pump for transferring ozone from said ozone generator to said contact lense container, said pump being located in said housing;
e) a switch located on said housing for operator activation;
f) means for sensing operation of said ozone generator and generating an ozone operating signal having at least two states;
g) means for sensing operation of said pump and generating a pump operating signal having at least two states; and,
h) control means for,
   1) activating said pump and said ozone generator in response to activation of said switch, and,
   2) deactivating said pump and said ozone generator in response to the states of said ozone generating signal and said pump generating signal.

16. The contact lense cleaning system according to claim 15 wherein said control means further includes:
a) clock means for determining elapsed time from activation of said pump and said ozone generator; and,
b) means for deactivating said pump and said ozone generator when the elapsed time is equal to a predetermined level.

17. The contact lense cleaning system according to claim 16 further including means for receipt of electrical power to said lense cleaning system, and wherein said control means further includes:
a) means for sensing a power failure to said contact lense cleaning system; and,
b) means for initalizing said clock means upon restoration of power to said contact leanse cleaning system.

18. The contact lense cleaning system according to claim 17 further including a non-volatile memory means and wherein said control means includes means for recording, in said memory means, usage data indicative of operation of said contact lense cleaning system.

19. The contact lense cleaning system according to claim 18 further including communication means for receipt of command data and transmission of usage data via a telephone line and wherein said control means includes means for transmitting said usage data from said memory in response to said command data.

20. The contact lense cleaning system according to claim 19 wherein said memory means further includes use counter data and wherein said control means includes:
a) means for, prior to activation of said pump and said ozone generator, comparing said use counter data with said usage data; and,
b) means for terminating operation if said usage data equals or exceeds said counter data.

21. A contact lense cleaning system having:
a) a housing;
b) an ozone generator for producing ozone, said ozone generator located within said housing;
c) a contact lense container being insertable into said housing having,
   1) a first valve being automatically sealed upon removal of said contact lense container from said housing, said first valve for receipt of ozone from said pump, and,
   2) a second valve being automatically sealed upon removal of said contact lense container from said housing, said second valve permitting excess ozone within said container to pass into the environment; and,
d) a pump for transferring ozone from said ozone generator to said contact lense container, said pump being located in said housing.

22. The contact lense cleaning system according to claim 21 wherein said contact lense container includes a sealable opening for putting contact lenses into said contact lense container.

23. The contact lense cleaning system according to claim 14 further including:
a) a liquid agent contained in said contact lense container; and,
b) a diffuser, located in said contact lense container, for diffusion of said ozone in said liquid agent.

24. The contact lense cleaning system according to claim 23 wherein said diffuser is a flat plate diffuser.

25. The contact lense cleaning system according to claim 14 wherein said ozone generator includes an ultraviolet lamp for generation of said ozone.

26. The contact lense cleaning system according to claim 25 wherein said ultraviolet lamp is U shaped and further including a chamber encircling said ultraviolet lamp, said chamber having a first end open for receipt of ambient air and a second end communicating with said pump.

27. The contact lense cleaning system according to claim 21 further including an ozone trap interposed between said second valve of said contact lense container and the environment.

28. A cleansing and sterilization mechanism comprising:
a) a housing having at least two slots therein;;
b) an ozone generator for producing ozone, said ozone generator located within said housing;
c) at least two containers being insertable into the slots of said housing;
d) a pump for transferring ozone from said ozone generator to a selected group of said at least two containers, said pump being located in said housing;
e) a switch located on said housing for operator activation;
f) sensing means for identifying which of said slots have a container therein and for generating slot occupation data indicative thereof; and,
g) control means for,
   1) activating said pump and said ozone generator in response to activation of said switch, and,
   2) for directing, in response to said slot occupation data, ozone to a selected group of said at least two containers.

29. The cleansing and sterilization mechanism according to claim 28 further including:
a) means for sensing operation of said ozone generator and generating an ozone operating signal having at least two states;
b) means for sensing operation of said pump and generating a pump operating signal having at least two states; and, wherein said said control means includes means for deactivating said pump and said ozone generator in response to the states of said ozone generating signal and said pump generating signal.

30. The cleansing and sterilization mechanism according to claim 29 wherein said control means further includes:
   a) clock means for determining elapsed time of ozone being delivered to each of said slots; and,
   b) means for discontinuing delivery of ozone to a slot when said slot's elapsed time is equal to a predetermined level.

31. The cleansing and sterilization mechanism according to claim 30 further including means for receipt of electrical power to said lense cleaning system, and wherein said control means further includes:
   a) means for sensing a power failure to said contact lense cleaning system; and,
   b) means for initalizing said clock means upon restoration of power to said contact leanse cleaning system.

32. The cleansing and sterilization mechanism according to claim 31 further including a non-volatile memory means and wherein said control means includes means for recording, in said memory means, usage data indicative of operation of said contact lense cleaning system.

33. The cleansing and sterilization mechanism according to claim 32 further including communication means for receipt of command data and transmission of usage data via a telephone line and wherein said control means includes means for transmitting said usage data from said memory in response to said command data.

34. The cleansing and sterilization mechanism according to claim 33 wherein said memory means further includes use counter data and wherein said control means includes:
   a) means for, prior to activation of said pump and said ozone generator, comparing said use counter data with said usage data; and,
   b) means for terminating operation if said usage data equals or exceeds said counter data.

35. The cleansing and sterilization mechanism according to claim 28 wherein each of said at least two containers includes:
   a) an resealable door for deposit of items to-be-cleaned into said container; and,
   b) status indicator means having at least two states and being visible to an operator, at least one of said states of said status indicator being in response to opening of said resealable door.

36. The cleansing and sterilization mechanism according to claim 35 wherein said control means includes means for changing states of said status indicator.

37. The cleansing and sterilization mechanism according to claim 36 wherein each of said containers includes:
   a) a first valve being automatically sealed upon removal of said contact lense container from said housing, said first valve for receipt of ozone from said pump; and,
   b) a second valve being automatically sealed upon removal of said contact lense container from said housing, said second valve permitting excess ozone within said container to pass into the enironment.

38. The cleansing and sterilization mechanism according to claim 28 further including:
   a) a liquid agent contained in said containers; and,
   b) a diffuser, located in each of said at least two containers, for diffusion of said ozone in said liquid agent.

39. The cleansing and sterilization mechanism according to claim 38 wherein the diffuser in each of said at least two containers includes at least one flat plate diffuser.

40. The cleansing and sterilization mechanism according to claim 28 wherein said ozone generator includes an ultraviolet lamp for generation of said ozone.

41. The cleansing and sterilization mechanism according to claim 40 wherein said ultraviolet lamp is U shaped and further including a chamber encirculing said ultraviolet lamp, said chamber having a first end open for receipt of ambient from said pump air and a second end communicating with the first valve of each of said at least two containers.

* * * * *